United States Patent [19]
Pezzoli et al.

[11] Patent Number: 5,735,402
[45] Date of Patent: Apr. 7, 1998

[54] SELECTION APPARATUS FOR POWDERS AND FINE PARTICULATE MATERIAL

[75] Inventors: Raffaele Pezzoli; Claudio Quarantelli, both of Parma, Italy

[73] Assignee: Protec S.r.l., Collecchio, Italy

[21] Appl. No.: 626,410

[22] Filed: Apr. 2, 1996

[30] Foreign Application Priority Data

Jul. 3, 1995 [IT] Italy .............................. PR95A0021

[51] Int. Cl.$^6$ ........................................... B03C 7/00
[52] U.S. Cl. .................... 209/129; 209/577; 209/587; 209/939
[58] Field of Search ................. 209/127.1, 127.3, 209/129, 576, 577, 587, 939

[56] References Cited

U.S. PATENT DOCUMENTS

| | | | |
|---|---|---|---|
| 3,977,526 | 8/1976 | Gordon et al. | 209/587 X |
| 4,186,836 | 2/1980 | Wassmer et al. | 209/587 X |
| 4,325,820 | 4/1982 | Whitlock | 209/129 X |
| 4,549,659 | 10/1985 | Hawkins et al. | 209/129 X |

*Primary Examiner*—David H. Bollinger
*Attorney, Agent, or Firm*—Birch, Stewart, Kolasch & Birch, LLP

[57] ABSTRACT

A selection machine and process for fine particulate material such as, for example, semolina wheat or other food or industrial products in powdery or granular form, where the particulate material is distributed on a continuous mobile support, is transported from the support to a scanning station for the identification in the particulate material, of undesirable parts thereof, and their position on the support, and, subsequently, to a sorting station having a photoconducting element that can be moved in synchronism with the support and on which photoconducting element is formed a latent image of electrostatic charges, corresponding to the position of the undesirable parts, which electrostatic charges separate the undesirable parts from the desired particulate material by electrostatic attraction.

15 Claims, 4 Drawing Sheets

SELECTION APPARATUS FOR POWDERS AND FINE PARTICULATE MATERIAL

BACKGROUND OF THE INVENTION

1. Field of the Invention

This invention relates to an apparatus and process for selecting and separating desired fine particulate material in food or industrial material and, generically, powders, from undesired material mixed or contained therein. Examples of fine particulate material include: semolina of wheat and of rice, or coffee or chocolate or other materials in the food field; the solid pigments used in the varnish and powders industry for sintered products, in the industrial field; and chemical components in powder form, in the pharmaceutical field.

2. Description of the Related Art

To sort particulate material having certain dimensions, one uses, as is known, optical survey systems that scan the particulate material which is distributed on a mobile bed and that, after identifying, in the particulate material, an undesirable portion of a particular position, control mobile aspiration systems, made up of a plurality of vacuum nozzles, which are operated selectively to remove the undesirable portions. A system of this type is described, for example, in U.S. Pat. No. 4,186,836.

Alternatively, the particulate material is made to flow, in a freefall, through an optical scanning station that selectively controls the blowing nozzles that are arranged downstream from the scanning station. These blowing nozzles selectively apply air or gas pressure to deflect the desirable or undesirable portions of falling material toward or away from a collection receptacle for that material.

These selection techniques, whether blowing or aspiration, cannot be used for fine particulate material for various reasons: because the particles are so similar in size and/or weight, it is difficult to determine which are the undesirable parts, in a freefall and to remove them by blowing or aspiration. The small dimensions of the particles also restrict the output of the selection process and, with mechanical and pneumatic means, it is impossible to isolate the individual particle that is to be separated from the contiguous or nearby particles.

To sort fine granular material and powders, the sorting systems currently used are based on certain predetermined physical characteristics that differentiate the undesirable parts from others, without identifying of the individual undesirable part.

For example, screening makes it possible to select particles that have different dimensions, as does floatation; centrifugation makes it possible to select particles that have differing specific weights; magnetic separation makes it possible to select particulate material as a function of its magnetic permeability, etc.

In the food industry, and in industry in general there are, however, many cases where these techniques are inadequate because the differentiation between the good product and the product to be discarded can be based only on the identification of generally optical properties, on the spatial identification of the parts to be discarded, and the removal of the product to be discarded requires using a local-action device, independent of any difference in a physical characteristic of the product to be discarded.

There is, therefore, an unsatisfied need to overcome the intrinsic limitations of selection systems by means of spatial identification of the product to be discarded and local removal of same, using mechanical devices such as pneumatic blowers or aspiration devices, which, when used for the selection of fine particulate material, can lead to unacceptable yields and very low productivity.

SUMMARY OF THE INVENTION

The selection apparatus for powders and fine particulate material according to the present invention, meets these requirements and solves these serious technical problems. Using this machine, the selective and local removal of undesirable parts is brought about by the forces of electrostatic attraction that are generated upon the particulate material, by means of electrical polarization of same by the local electrical field, developed by electrical charges formed selectively on the surface of a load-carrying element, facing a mobile bed to support the material to be sorted and synchronized with the element that carries the electrical charges.

More specifically, the objects and advantages of the present invention are achieved by an apparatus for sorting particulate material containing desirable and undesirable components, and removing undesirable components therefrom, comprising:

(A) mobile support means for supporting and transporting said particulate material on a surface thereof;

(B) means for determining and indicating the presence and position of said undesirable components on said mobile support means;

(C) means for removing said undesirable components from said mobile support means, comprising:

(1) a photoconducting means capable of moving in a manner synchronized with the motion of said mobile support means, comprising a photoconducting surface having a position thereon corresponding to a position on said mobile support means;

(2) electrostatic charge means for providing an electrostatic charge to said photoconducting surface;

(3) latent image generation means for generating a latent image of electrostatic charges on said photoconducting surface at one or more positions thereon corresponding to one or more positions on said mobile support means;

wherein said photoconducting means is disposed relative to said mobile support means such that said latent image on said photoconducting surface and the corresponding position on said mobile support means come into sufficiently close proximity that particulate material located at said position on said mobile support means are attracted by, and move to, said photoconducting surface; and (4) means for removing particulate material from said photoconducting surface.

The selection process may, in some ways, be considered to be similar to the process used in electrophotographic printers. The material to be sorted is spread out uniformly on a mobile support, similar to the developer roller of an electrophotographic printer, and is scanned by suitable means, which are in themselves known and which determine the presence, on the support, of undesirable parts, as well as their position. In the course of its movement, the support is juxtaposed to a latent image carrier, consisting, for example, of a cylinder with a surface made of photoconducting material.

The latent image consists of electrical charges, arranged according to a representative configuration, in a positive or negative form, of the position of the undesirable parts and is formed by processes well known in the field of electrophotographic printing.

If the image is a positive latent image, the undesirable parts of the particulate material, which are juxtaposed to the latent image carrier, are attracted to the surface of the latent image carrier and are removed from the mobile support.

If the latent image is a negative latent image, it is the particulate material, devoid of undesirable parts, that is attracted to the surface of the latent image carrier.

The material that is attracted to the surface of the latent image carrier is then separated from the former by means therefore, for example, a cleaning blade, a rotating brush, and/or blowing/aspirating systems.

A selection machine of this type can sort even extremely fine particulate material at great speed, with a very high selection output, correlated to the very high resolution (as much as 600 dpi) with which the latent image can be formed.

In practice, since the resolution of the process, on the one hand, and the velocity of the process (and hence, the productivity of the process), on the other hand, are somewhat antithetical terms, it may be convenient, in some cases, to reduce the resolution of the latent image to the detriment of the selection performance and to the benefit of productivity.

According to a another embodiment of this invention, an apparatus of the type described performs a sorting of the particulate material by removing the undesirable parts that are fractionated into classes.

In this embodiment, scanning means are provided which, in addition to recognizing the presence of undesirable parts and their spatial position on the mobile support, identify the membership of the various undesirable parts in one of a plurality of classes.

Depending on the membership of the undesirable parts in the various classes, there is generated, on a plurality of latent image carriers, a plurality of latent images, one per carrier, each correlated to a certain class of undesirable parts.

In this way, it is possible to remove separately the various classes of undesirable parts from the particulate material with a "differentiated collection," facilitating the possible reuse or recycling of the discards for various applications.

More specifically, the present invention relates to another embodiment of an apparatus for sorting particulate material containing desirable and undesirable components, and removing undesirable components therefrom, comprising:

(A) mobile support means for supporting and transporting said particulate material on a surface thereof;

(B) means for scanning said surface of said support to determine and indicate the presence and location of undesirable components on said surface of said mobile support means;

(C) means for removing said undesirable components from said mobile support means, comprising:

(1) means for determining whether an component is a member of one or more predefined classes of undesirable material;

(2) means for indicating whether said component is a member of said class, and means for indicating a position of said component on said mobile support;

(3) a photoconducting means corresponding to each of said classes of material, capable of moving in a manner synchronized with the motion of said mobile support means, comprising a photoconducting surface having a position thereon corresponding to a position on said mobile support means;

(4) an electrostatic charge means corresponding to said photoconducting means, for providing an electrostatic charge to said photoconducting surface or surfaces;

(5) a latent image generation means for generating a latent image of electrostatic charges on each of said photoconducting surfaces at one or more positions thereon corresponding to one or more positions on said mobile support means;

wherein each of said photoconducting means is disposed relative to said mobile support means such that each of said latent images on said photoconducting surface and the corresponding position of material on said mobile support means come into sufficiently close proximity that particulate material located at said position on said mobile support means is attracted by, and moves to, said photoconducting surface; and (4) means for removing particulate material from said photoconducting surface.

The present invention also relates to a process for sorting particulate material containing desirable and undesirable components, and removing undesirable components therefrom, comprising:

(A) supplying particulate material containing desirable and undesirable components to a scanning station;

(B) scanning said particulate material to determine the presence and location of said undesirable components, and providing a signal to a controller indicating said presence and location of said undesirable components;

(C) sorting said particulate material, comprising:

(1) providing an electrostatic charge on a photoconducting surface, wherein said photoconducting surface contains a point corresponding to each possible location of said particulate material, and wherein said photoconducting surface is moveable in a manner synchronized with the movement of said particulate material;

(2) creating a latent image on said photoconducting surface corresponding to a location of said particulate material, based upon information provided by said controller;

(3) bringing said photoconducting surface into sufficiently close proximity to said particulate material that said particulate material at a position corresponding to said latent image is attracted by, and moves to, said photoconducting surface; and (4) removing said particulate material from said photoconducting surface.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The characteristics and advantages of the invention will emerge more clearly from the following nonlimiting description of a preferred embodiment and its variants, given with reference to the attached drawings, where.

DETAILED DESCRIPTION OF THE INVENTION

Figure 1:
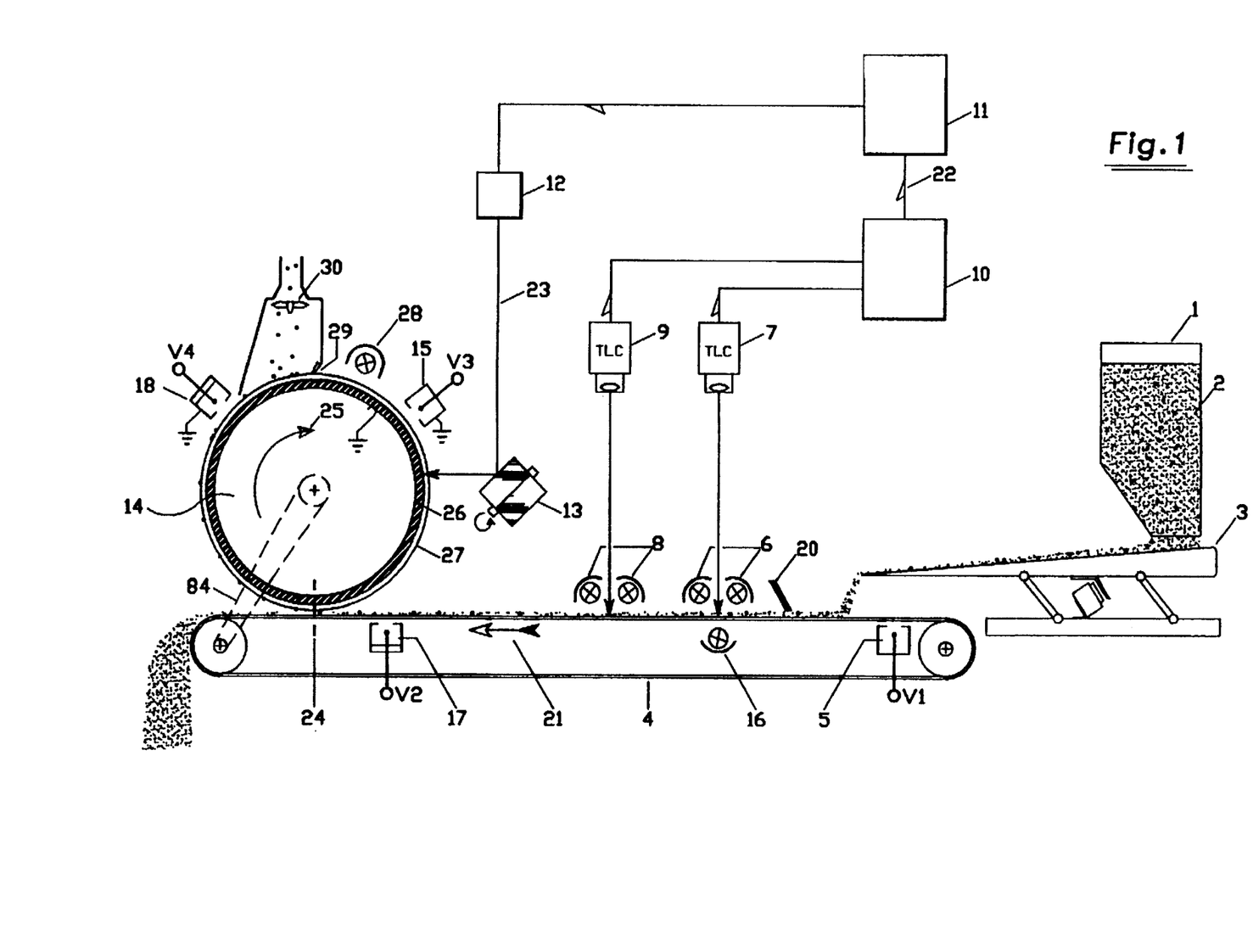
FIG. 1 is an overall diagram showing a preferred embodiment of the sorting machinery.

With reference to FIG. 1, a preferred embodiment of the selection machine for powders in accordance with this invention comprises a hopper containing powder to be sorted 2, which is deposited by discharging the hopper, in a monitored quantity, upon a vibrating surface 3 that provides for the uniform distribution of the product.

The vibrating surface deposits the powder on the upper face of an endless conveyor belt 4 that runs at the proper speed, for example, 1 to 2 meters per second, indicated by arrow 21.

Where necessary, a scraping knife 20 forms a single layer of granules on belt 4. Although the conveyor belt is shown as being horizontal, it can also be inclined.

If the weight of the material and the possible surface roughness of the conveyor belt are not sufficient to ensure the stability of the material in position on the belt, provision can be made, as illustrated, for an electrostatic load cororator or corotron 5 that forms a uniformly distributed charge on the lower face of the belt, immediately upstream of the scraping knife 20. In this case, belt 4 is suitably flexible and made of insulating material, with a low dielectric constant, so that the electrical fields, generated by the deposited charge, will effectively attract powders 2 on the belt surface, stabilizing the powder in position. Corotron 5 is supplied with a suitable voltage V1, for example, on the order of −2 kv, with relation to the mass, to raise the lower face of the belt to a suitable potential—for example—on the order of −300v, and that is a function of the material to be treated. It is obvious that corotron 5 can be replaced by a conducting rubber roller or by a metal brush which, in this case, are supplied with a suitable voltage to achieve the same effect.

It may be necessary to monitor and regulate the voltage supply to corotron 5 and/or also to the other corotrons used in the process (15, 17, 18), as a function of the humidity percentage present in the product to be sorted.

The formation of the charge on the lower face of the conveyor belt may be facilitated by an anodic field plate, connected to the ground and facing the transportation surface, opposite corotron 5, or the roller or brush.

Scraping knife 20, corotron 5, and the discharge edge of vibrating surface 3 define a loading station through which conveyor belt 4 passes during its continuous movement.

From the loading station, the particulate material, which is distributed uniformly over the conveyor belt, is transported to a scanning or reading station where a reading system, which may be of a known type, identifies possible defects in the particulate material and, hence, undesirable parts 90 of the product.

The reading system comprises, e.g., an illuminating group 6 that illuminates a transverse section of the conveyor belt with a light having a predetermined frequency or a combination of predetermined frequencies, and a remote camera 7 or solid-state sensor that acquires the image of the moving product, in the simplest case, merely by means of the rows running transverse to the direction of the conveyor belt 4 movement.

The acquisition of the image is synchronized with the movement of the conveyor belt; in other words, the image of each row is correlated with the position of the row on the conveyor belt so that it is possible to know the position of the same row at any successive instant as a function of the running speed of the conveyor belt.

For special types of powders to be sorted 2, it is possible to introduce, inside conveyor belt 4, an illuminating source 16, having characteristics similar to those of illuminating group 6, to increase the contrast of the undesirable parts 90.

Provision may be made, as shown in FIG. 1, for a multiple reading system, comprising a second illuminating group 8 with a wavelength different from that of the first one and a second remote camera. This is done to spot diverse defects that are evidenced only under particular and distinct illumination conditions.

It is clear, however, that the same effect could be achieved by using wide-spectrum light and filters associated with several remote cameras.

The signals from remote cameras 7 and 9 are sent to a processing unit 10, of the conventional type that is available on the market, which transmits suitable processing algorithms, identifies all of the granules of the particulate material which, by virtue of dimension and/or color and/or shape and/or reflectivity, do not correspond to the desired product and must be discarded.

At its output, on a channel 22, the processing unit generates properly timed command signals that are representative of the spatial position, on the conveyor belt, of defective parts that are to be discarded.

These signals, suitably amplified, in the known state of the art, control electromechanical and electropneumatic devices for the aspiration extraction of defective parts to be discarded.

According to this invention, the output signals coming from the processing unit are applied to an electronic modulation logic unit 11, of the type commonly employed in electrophotographic printers, more commonly known as laser printers.

Unit 11 controls laser diode 12, preferably with a modulation device of ON-OFF type, whose light beam 23, properly collimated, is deflected by a rotating mirror 13 toward the surface of a mobile element 14, generally having the shape of a rotating drum, or other deflection systems, which, by virtue of the function it performs, is called a latent image carrier or a photoconducting roller in electrophotographic technology.

Mirror 13 (which is in fact, a rotating prism with several mirror rollers) deflects light beam 23 along a generatrix of the rotating drum, so that, due to the combined effect of scanning light beam 23 and the rotation of drum 14, the entire cylindrical surface of drum 14 will be scanned.

Replacing laser diode 12 and mirror 13, it is well known that one can use a row or matrix of photo-emitting diodes, controlled individually (LED ARRAY), arranged along a generatrix of drum 14.

Drum 14 is positioned, with relation to conveyor belt 4 that carries the particulate material, in such a way that one of its generatrixes, pertaining to the sorting station 24, will be faced in close proximity by conveyor belt 4, at a distance which, according to the grain size of the particulate material, can vary from several tenths of a micron up to several millimeters.

Drum 14 is mechanically coupled to the conveyor belt 4 activating device by a mechanical transmission 84, so that the drum will rotate in the direction indicated by arrow 25, at a peripheral speed that is exactly equal to the forward movement speed of conveyor belt 4.

It is thus evident that, unambiguously, one point and only one point on the surface of the drum corresponds to every point on the upper surface of the conveyor belt, and that these points are juxtaposed in correspondence to the generatrix of sorting station 24.

Along the passageway of conveyor belt 4, the generatrix of sorting station 24 defines a position which, in electrophotographic printing technology, is called a developing station, which, in this application, can be called a sorting station.

Drum 14 consists of a conducting cylindrical element 26, generally made of metal, picked at a predetermined (generally ground) potential, on whose outer surface is formed a photoconducting layer 27.

The following are arranged, along the periphery of the drum, in inverse order with relation to its direction of rotation and up-line from the generatrix that is scanned by light beam 23:

- a crown-effect electrostatic charge generator or corotron 15, supplied with a voltage V3 (for example, −2 kv) which uniformly charges the surface of the photoconductor at a predetermined potential, for example, −700v;
- a normalizing (quenching) lamp 28 that, by activating the photoconductor, discharges it, thus bringing it to a potential that is very close to the potential of conductor 26—in other words, the ground potential; scraping and cleaning knife 29 of the drum, associated with an aspirating hood 30;
- an optional electrostatic charge generator or corotron 18, supplied with a voltage V4, having a sign opposite to V3, in order to at least partly neutralize any residual electrical charge present on the photoconductor, thereby facilitating the separation of the particulate material present there.

When a corotron 5 is employed to stabilize the solid particulate material distributed over conveyor belt 4, the apparatus also contains another electrostatic charge generator or corotron 17, in proximity to sorting station 24, supplied with a voltage V2, to at least partly neutralize the electrical charge that is applied to conveyor belt 4 and to promote the removal of the solid particulate material from conveyor belt 4.

The embodiment of the apparatus thus described works as discussed below.

As the solid particulate material, transported by conveyor belt 4, gradually passes through the scanning station, the spatial position of the identified defects on the conveyor belt, determined as a coordinate on a line transverse to the direction of travel of the belt, is stored by processing unit 10. The processing unit, after a suitable delay (which is determined by the difference between the time necessary for the scanned conveyor belt to pass from the scanning station to sorting station 24 and the time necessary for the generatrix of drum 14, scanned by the light scanning beam, to reach the sorting station) quenches the light scanning beam, corresponding to the position of the defects.

Downstream from the generatrix of drum 14, which is scanned by beam 23, there is thus formed a latent positive image that is representative of the defects and that is made up of electrical charges, arranged on photosensitive surface 27, at the points corresponding to the spatial position of the defects of the particulate material on the conveyor belt.

When the particulate material arrives at sorting station 24, the defective and undesirable part is attracted electrostatically by the electrical field that is locally generated by the electrical charges of the latent image, and is removed from conveyor belt 4 to adhere to the surface of drum 14.

Purified of undesirable parts 90, the particulate material proceeds along conveyor belt 4 so as to be discharged, also nearly by the effect of gravity, into a suitable collector.

Undesirable parts 90, transported by drum 14, appear, if present, under corotron 18, which neutralizes the residual electrostatic charges, and proceed all the way to aspiration hood 30, where scraping knife 29 removes them from the surface of the drum to permit their aspiration.

The subsequent quenching lamp 28 ensures the suppression of any residual charge of the photosensitive layer to present it again at the loading station formed by corotron 15, under predetermined conditions, so as to permit the continuous repetition of the process.

It is clear that the sorting process can be based not only on the formation of a latent image of the positive type (where the electrical charge, left on the photoconducting material, represents the defects), but also on the formation of a latent image of the negative type, in which the electrical charge, left on the photoconducting material, represents the particulate material that is devoid of any defects and where the defects are represented by the absence of a charge.

In this case, the undesirable parts 90 are left on conveyor belt 4 at the sorting station, and they are discharged from said conveyor belt while the particulate material, that has been cleansed of any defects, is "captured" by drum 14 and adheres thereto.

The first alternative is preferable for some uses, as will be discussed later.

It is thus evident that the sorting process used here is very similar to an electrophotographic printing processes and, also similarly, can benefit from many of the technical devices and multiple process and structural implementation variants that have been developed for electrophotographic printing, so as to adapt the apparatus to specific sorting and separation requirements, dictated by the various materials to be sorted.

Some of these variants are shown below.

Figure 2:
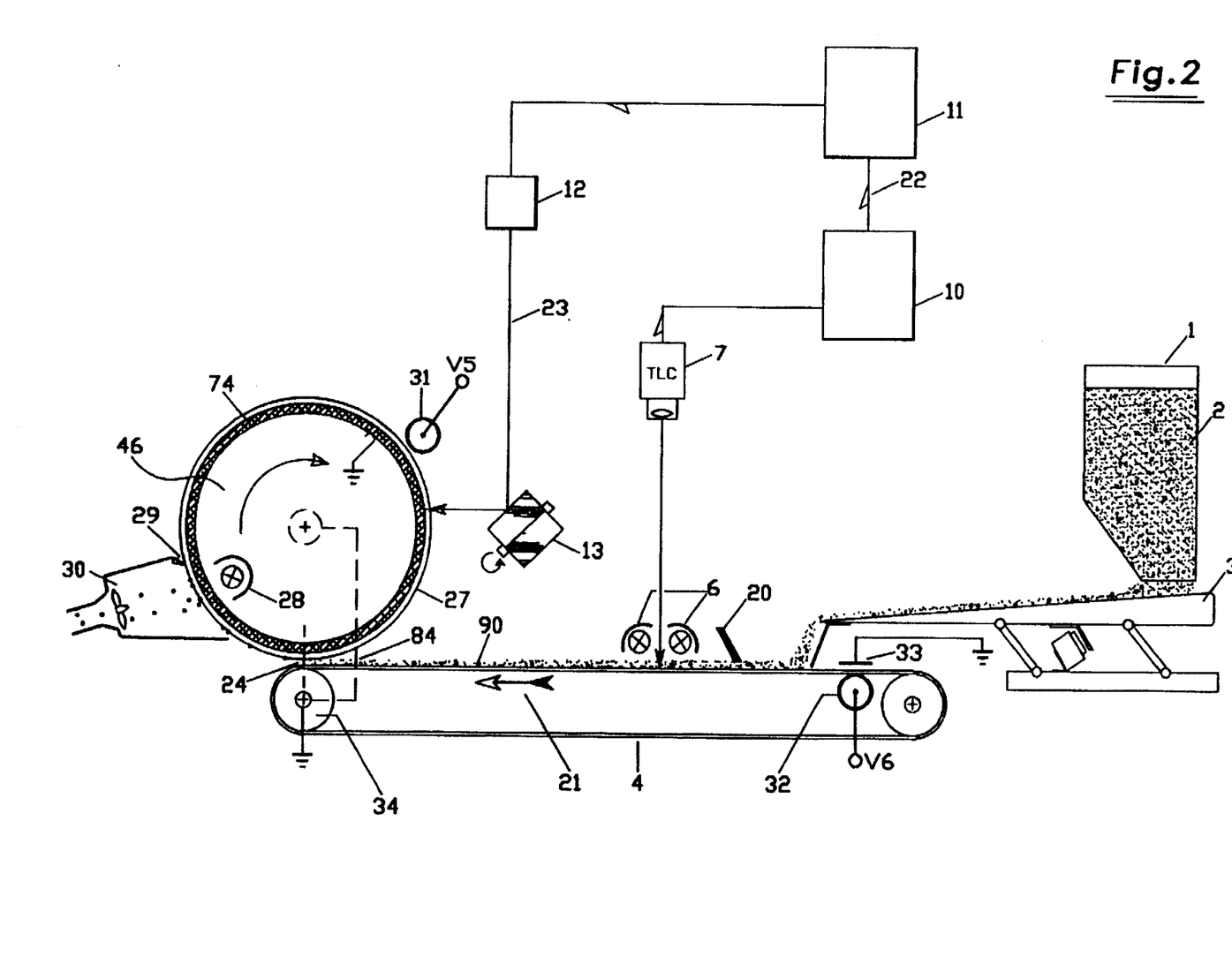
FIG. 2 is an overall diagram showing a first embodiment variant of the machinery in FIG. 1.

FIG. 2 shows an embodiment of the sorting machine where all of the crown-effect electrostatic dischargers or corotrons, which to some extent generate ozone, are completely eliminated and replaced by non-ionizing electrostatic charge generators. Because the machinery in FIG. 2 differs from that in FIG. 1 only in some respects, functional elements in FIG. 2 equivalent to those in FIG. 1 are identified by the same reference numbers, and any detailed description of the machinery and its operation, which are substantially identical to those in FIG. 1, is omitted.

In FIG. 2, the corotron 5, from FIG. 1, is replaced by a conducting rubber roller 32, which is located opposite a grounded field armature 33. The roller is polarized by a voltage source V6 for applying an electrical charge to conveyor belt 4.

The electrical charge, formed on conveyor belt 4, is discharged at the sorting station by a conductor roller 34 which is grounded, and which, in a suitable manner, acts as a moving roller for conveyor belt 4.

Corotron 15, in FIG. 1, is replaced in FIG. 2 by a conducting rubber roller 31, which is polarized by voltage V5.

Finally, by using a cylindrical conducting element 74, made of transparent or translucent conducting material by substituting a metallic cylindrical element, quenching lamp 28 can be housed inside the drum corresponding to the aspiration hood 30, and can perform both the function of quenching the photoconductive layer 27 and the function of charge neutralization performed by corotron 18 in FIG. 1.

To permit the selective sorting of undesirable parts 90, which are grouped in different defect classes, one may use a plurality of removal means—in other words, complexes, such as drum 14, laser diode 12, and modulation unit 11, as shown in FIG. 1.

Figure 3:
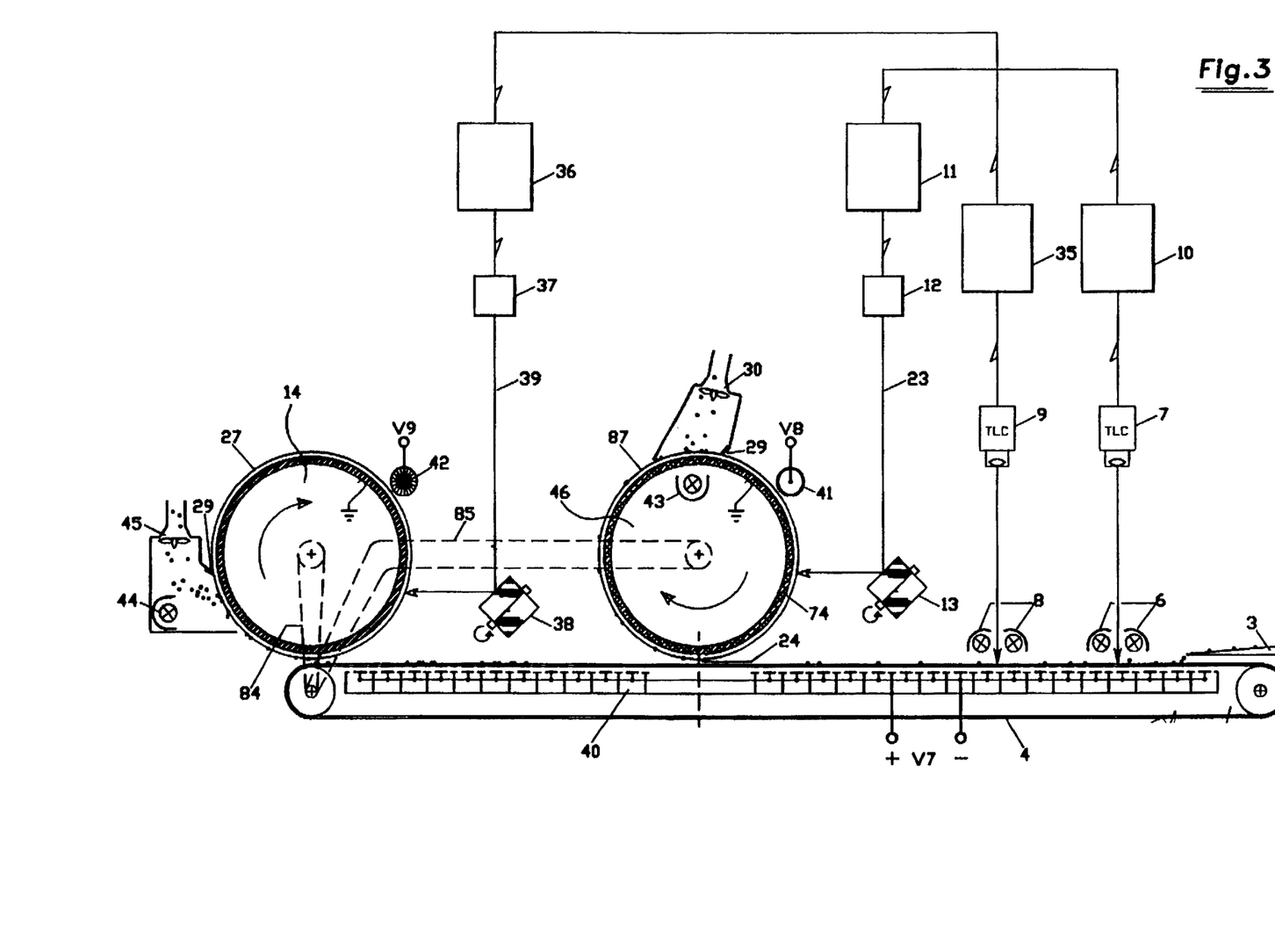
FIG. 3 is an overall diagram showing a preferred embodiment of the sorting machinery in accordance with this invention, capable of performing a sorting operation for distinct or separate classes.

An apparatus that meets this requirement is shown in FIG. 3: two distinct reading systems, 6,7 and 8,9, send reading signals to two distinct processing units 10, 35, which, in turn, control two distinct modulation units 11, 36, each made up of a laser diode 12, 37.

By means of a deflecting mirror 13, 38, each of the laser diodes forms a latent image on photosensitive surface layers 27, 87, respectively, of each of the two drums 14, 46, that carry latent images, which, together with conveyor belt 4, define two distinct and methodically successive sorting stations.

In this case, the latent image, formed on drum 14, is necessarily of the positive type and identifies the position of a first class of defects.

The latent image on drum 46, of either the positive or negative type, identifies a second class of defects in position.

In this way, drum 14 picks up and removes a first class of undesirable parts 90 and drum 46 separates a second class of undesirable parts 90 from the particulate material.

It is obvious that the differentiation operation between the two classes of defects can also be performed, in many practical applications, by a single processing unit that controls a plurality of optical modulation units, and that, in the situation, one reading system alone may suffice.

For example, in this embodiment shown in FIG. 3, the two drums 14, 46, are connected mechanically to conveyor belt 4 by a mechanical transmission 84, 85. The latter can be replaced by an electronic movement synchronization systems.

The other variants shown in FIG. 3 are examples of the wide range of technical solutions offered by the machinery.

To stabilize—whenever necessary—the product on conveyor belt 4, one may use a double grid 40 of interlaced electrodes, among which is applied a suitable voltage V7.

Where a flexible dielectric layer is interposed, the electrodes are arranged so as to face toward the lower side of conveyor belt 4, along the entire run from the loading station up to the last sorting station, with the exception of the intermediate sorting station.

On the upper face of the conveyor belt, these electrodes generate a spatially alternating electrical field that exerts a pulsating electrostatic attraction force (by way of electrical polarization) upon the solid particulate material.

The electrostatic charge generators on the photosensitive surface of drums 14, 46 may be either conducting rubber rollers 41, polarized electrically by an applied voltage V8, or may be rotating brushes 42, which are electrically polarized by an applied voltage V9.

The quenching lamp may be inside the drum if the latter is transparent, as shown by quenching lamp 43 and drum 14 in FIG. 3, or it may be outside if the latter is opaque. Moreover, if the drum is opaque, the quenching lamp can also be inside an aspiration hood, as shown by drum 46, quenching lamp 44, and aspiration hood 45 in FIG. 3.

In the preceding examples, reference was always made to a continuous conveyor belt and to a cylindrical removal drum. But it is evident that the removal drum, or removal drums, can be replaced by an endless belt or belts made up of a conducting support that is possibly transparent and upon which a photoconducting layer is superimposed. By the same token, endless belt 4 can be replaced by a mobile supporting element for particulate material in a cylindrical shape.

Figure 4:
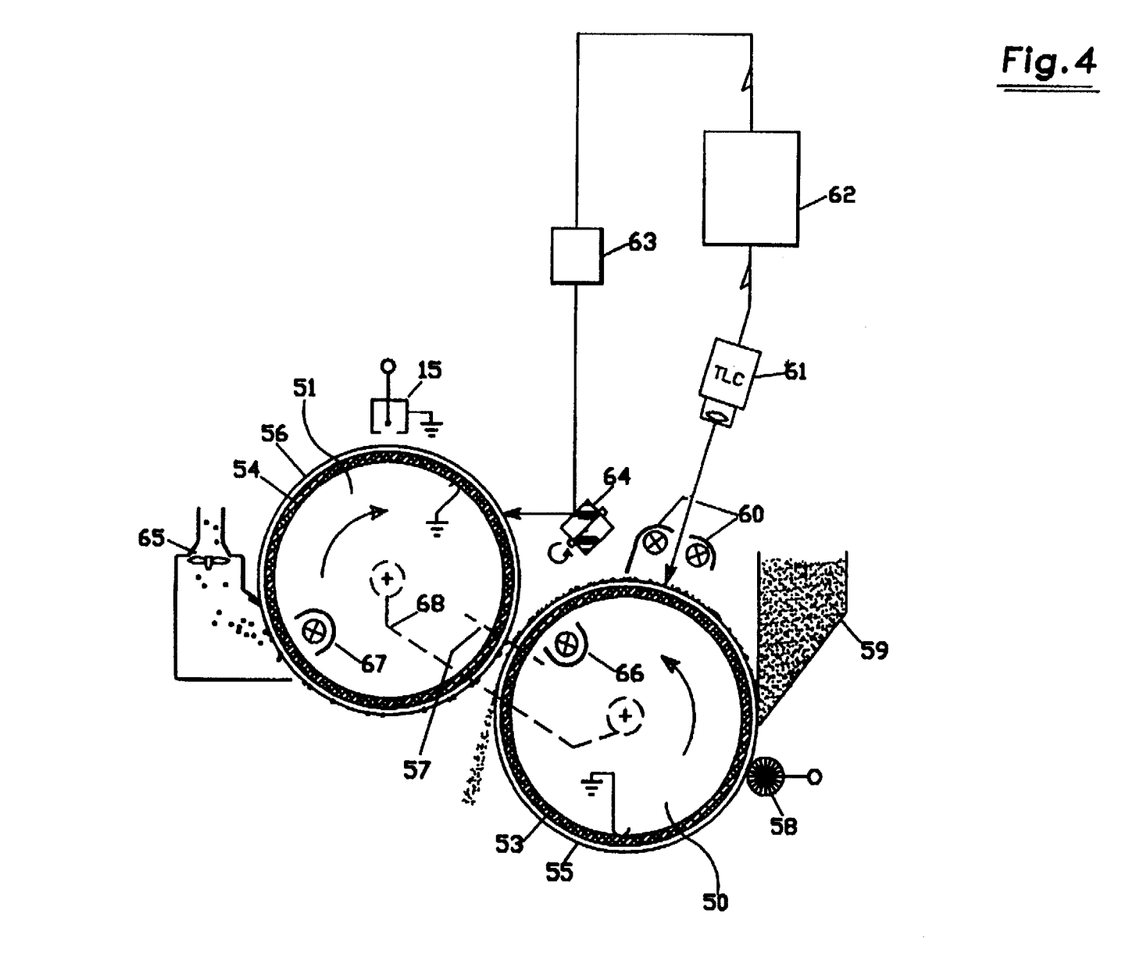
FIG. 4 is an overall diagram showing a second embodiment variant of the machinery shown in FIG. 1.

FIG. 4 shows a sorting apparatus in which both mobile transport 50 for particulate material and mobile removal element 51 are made up of two center rotating cylindrical drums. Both drums 50 and 51 are suitably made up of a transparent conducting support 53, 54, on which a photoconducting layer 55, 56, is superposed.

The two drums are juxtaposed at a suitable distance from each other, along a generatrix 57 that defines a sorting station, and are linked mechanically to the movement device of a mechanical transmission 84, so that the peripheral speeds of the two drums will be equal and synchronized.

The conducting support of the two drums is suitably polarized at a suitable potential—for example, a ground potential.

A brush 58 or some other equivalent means electrically charges the surface of drum 50, and a loading hopper 59 distributes, on the surface of drum 50, a uniform layer of particulate material that adheres to the surface of the drum. In the course of its rotation movement, drum 50 exposes the particulate material to a reading system 61 that is connected to a defect and modulation recognition unit 62 that controls a selective illumination system 63, 64 for a generatrix of drum 51 and for the formation of a latent image on its surface. During their passage to sorting station 57, undesirable parts 90 of the particulate material are attracted to the surface of drum 51 and are conveyed to a collecting chamber 65.

To facilitate the migration of the undesirable parts 90 from drum 50 to drum 51 and from drum 51 to collecting chamber 65, there is provided, inside drum 50, a charge neutralization and quenching lamp 66, immediately up-line from sorting station 57, and inside drum 51, there is a lamp 67 which has the same function.

Obviously, in machinery of this type, the reading system must operate in a spectral field to which the photoconducting material is insensitive, or at brightness levels that are insufficient to neutralize the charge formed on the photoconducting material, or the particulate material itself must, through its opacity, furnish an adequate screen against radiation.

It is also clear that the latent image, formed on drum 51, can be negative, and that provision can be made for a third drum, arranged tandem to the second one, so as to form a second latent image on it with a suitable potential to track a distinct sorting operation for classes of defects.

In the above description, reference was made to the sole phenomenon of electrical and dielectrical polarization of the particulate material, immersed in an electrical field, as causing the electrostatic forces exerted upon the particulate material. But it is evident that, in many practical applications, it is also possible, as in electrophotography, to induce an electrical charge directly upon the particulate material by the triboelectric effect, and to use the repulsion and attraction forces that are exerted among the electrical charges with an equal or opposite sign so as to obtain the selective attraction or repulsion of the particulate material from a suitably electrically polarized support toward another removal element on which is formed a latent image, consisting of selectively placed electrostatic charges.

The invention being thus described, it will be clear that the same may be varied in many ways. Such variations are not to be regarded as a departure from the spirit and scope of the invention, and all such modifications as would be obvious to one skilled in the art are intended to be included within the scope of the following claims.

What is claimed is:

1. An apparatus for sorting particulate material containing desirable and undesirable components, and removing undesirable components therefrom, comprising:

(A) mobile support means for supporting and transporting said particulate material on a surface thereof;

(B) means for determining and indicating the presence and position of said undesirable components on said mobile support means;

(C) means for removing said undesirable components from said mobile support means, comprising:
  (1) a photoconducting means capable of moving in a manner synchronized with the motion of said mobile support means, comprising a photoconducting surface having a position thereon corresponding to a position on said mobile support means;
  (2) electrostatic charge means for providing an electrostatic charge to said photoconducting surface;
  (3) latent image generation means for generating a latent image of electrostatic charges on said photoconducting surface at one or more positions thereon corresponding to one or more positions on said mobile support means;
  wherein said photoconducting means is disposed relative to said mobile support means such that said latent image on said photoconducting surface and the corresponding position on said mobile support means come into sufficiently close proximity that particulate material located at said position on said mobile support means are attracted by, and move to, said photoconducting surface; and
  (4) means for removing particulate material from said photoconducting surface.

2. The apparatus according to claim 1, wherein said latent image is a positive latent image, is generated at a position on said electroconducting surface corresponding to a position of said undesirable components on said mobile support surface, and wherein said particulate material moving to said photoconducting material is said undesirable components.

3. The apparatus according to claim 1, wherein said latent image is a negative latent image, is generated at a position on said electroconducting surface corresponding to a position of said desirable components on said mobile support surface, and wherein said particulate material moving to said photoconducting material is said desirable components.

4. The apparatus according to claim 1, wherein:
said photoconducting means comprises a rotating cylindrical drum comprising a photoconducting layer disposed upon an outer surface of an internal transparent conducting layer; and
said removal means comprises a lamp means for irradiating and neutralizing said photoconducting layer in a vicinity near said lamp means.

5. The apparatus according to claim 4, wherein said lamp means is disposed inside said rotating cylindrical drum, and irradiates said photoconducting layer through said internal transparent conducting layer.

6. The apparatus according to claim 1, further comprising a means for loading said particulate material onto said mobile support means;
wherein said mobile support means comprises:
  (a) means for forming an electric field on said surface thereof; and
  (b) means for neutralizing said electric field disposed at a location on said mobile support means upstream of said means for determining and indicating the presence and position of said undesirable components on said mobile support means.

7. An apparatus for sorting particulate material containing desirable and undesirable components, and removing undesirable components therefrom, comprising:
  (A) mobile support means for supporting and transporting said particulate material on a surface thereof;
  (B) means for scanning said surface of said support to determine and indicate the presence and location of undesirable components on said surface of said mobile support means;
  (C) means for removing said undesirable components from said mobile support means, comprising:
    (1) means for determining whether an component is a member of one or more predefined classes of undesirable material;
    (2) means for indicating whether said component is a member of said class, and means for indicating a position of said component on said mobile support;
    (3) a photoconducting means corresponding to each of said classes of material, capable of moving in a manner synchronized with the motion of said mobile support means, comprising a photoconducting surface having a position thereon corresponding to a position on said mobile support means;
    (4) an electrostatic charge means corresponding to said photoconducting means, for providing an electrostatic charge to said photoconducting surface or surfaces;
    (5) a latent image generation means for generating a latent image of electrostatic charges on each of said photoconducting surfaces at one or more positions thereon corresponding to one or more positions on said mobile support means;
  wherein each of said photoconducting means is disposed relative to said mobile support means such that each of said latent images on said photoconducting surface and the corresponding position of material on said mobile support means come into sufficiently close proximity that particulate material located at said position on said mobile support means is attracted by, and moves to, said photoconducting surface; and
    (4) means for removing particulate material from said photoconducting surface.

8. The apparatus according to claim 7, wherein said latent image is a positive latent image, is generated at a position on said electroconducting surface corresponding to a position of a member of said class of undesirable components on said mobile support surface, and wherein said particulate material moving to said photoconducting material is said member of said class of undesirable components.

9. The apparatus according to claim 7, wherein said latent image is a negative latent image, is generated at a position on said electroconducting surface corresponding to a position of said desirable components on said mobile support surface, and wherein said particulate material moving to said photoconducting material is said desirable components, and said class of undesirable components is left on said mobile support means.

10. The apparatus according to claim 7, wherein:
said photoconducting means comprises a rotating cylindrical drum comprising a photoconducting layer disposed upon an outer surface of an internal transparent conducting layer; and
said removal means comprises a lamp means for irradiating and neutralizing said photoconducting layer in a vicinity near said lamp means.

11. The apparatus according to claim 10, wherein said lamp means is disposed inside said rotating cylindrical drum, and irradiates said photoconducting layer through said internal transparent conducting layer.

12. The apparatus according to claim 7, further comprising a means for loading said particulate material onto said mobile support means;

wherein said mobile support means comprises:
- (a) means for forming an electric field on said surface thereof; and
- (b) means for neutralizing said electric field disposed at a location on said mobile support means upstream of said means for determining and indicating the presence and position of said undesirable components on said mobile support means.

13. A process for sorting particulate material containing desirable and undesirable components, and removing undesirable components therefrom, comprising:

(A) supplying particulate material containing desirable and undesirable components to a scanning station;

(B) scanning said particulate material to determine the presence and location of said undesirable components, and providing a signal to a controller indicating said presence and location of said undesirable components;

(C) sorting said particulate material, comprising:
- (1) providing an electrostatic charge on a photoconducting surface, wherein said photoconducting surface contains a point corresponding to each possible location of said particulate material, and wherein said photoconducting surface is moveable in a manner synchronized with the movement of said particulate material;
- (2) creating a latent image on said photoconducting surface corresponding to a location of said particulate material, based upon information provided by said controller;
- (3) bringing said photoconducting surface into sufficiently close proximity to said particulate material that said particulate material at a position corresponding to said latent image is attracted by, and moves to, said photoconducting surface; and
- (4) removing said particulate material from said photoconducting surface.

14. The process according to claim 13, wherein said latent image is a positive latent image, is generated at a position on said electroconducting surface corresponding to a position of said undesirable components, and wherein said particulate material moving to said photoconducting material is said undesirable components.

15. The process according to claim 13, wherein said latent image is a negative latent image, is generated at a position on said electroconducting surface corresponding to a position of said desirable components, and wherein said particulate material moving to said photoconducting material is said desirable components.

* * * * *